United States Patent [19]

Brown

[11] Patent Number: 4,520,160

[45] Date of Patent: May 28, 1985

[54] ORGANOPOLYSILOXANE EMULSIFIER COMPOSITIONS AND METHOD THEREFOR

[75] Inventor: Paul L. Brown, Saginaw, Mich.

[73] Assignee: Dow Corning Corporation, Midland, Mich.

[21] Appl. No.: 565,554

[22] Filed: Dec. 27, 1983

[51] Int. Cl.³ .................................................. C08K 5/05
[52] U.S. Cl. ...................................... 524/765; 528/15;
528/31; 528/25; 528/26; 556/445; 556/446;
556/451; 556/462; 556/436
[58] Field of Search ............... 556/445, 446, 451, 462,
556/436; 524/765; 528/25, 26, 31, 15

[56] References Cited

U.S. PATENT DOCUMENTS

| | | | |
|---|---|---|---|
| 3,042,192 | 9/1968 | Haluska | 260/448.2 |
| 3,629,308 | 12/1971 | Bailey et al. | 260/448.2 |
| 4,122,029 | 10/1978 | Gee et al. | 252/309 |

FOREIGN PATENT DOCUMENTS 51-33600  9/1976  Japan .

Primary Examiner—Melvyn I. Marquis
Attorney, Agent, or Firm—George A. Grindahl

[57] ABSTRACT

Siloxane-oxyalkylene block copolymer compositions are prepared by a hydrosilylation reaction, using a saturated higher alcohol, such as isostearyl alcohol, as the reaction solvent. The reaction solvent need not be removed from the resulting block copolymer, particularly when the block copolymer is used as an emulsifier in personal care compositions.

6 Claims, No Drawings

ORGANOPOLYSILOXANE EMULSIFIER COMPOSITIONS AND METHOD THEREFOR

BACKGROUND OF THE INVENTION

The present invention relates to an improved method for preparing organopolysiloxane-polyoxyalkylene block copolymers, also referred to herein as siloxane-oxyalkylene copolymers, and to the compositions obtained thereby. More specifically, this invention relates to an improved hydrosilylation method for preparing siloxane-oxyalkylene copolymers consisting of one or more organopolysiloxane blocks bonded to one or more polyoxyalkylene blocks by one or more silicon-carbon bonds.

The preparation of siloxane-oxyalkylene copolymers by way of a hydrosilylation reaction between an organohydrogenopolysiloxane and an olefinically substituted polyoxyalkylene is well known. For one reason or another, such as to aid in handling the reactants or to moderate an exothermic reaction or to promote solubility of the reactants, the hydrosilylation reaction is typically conducted in a hydrocarbon solvent such as benzene, toluene or xylene. In these cases the hydrocarbon solvent is usually removed from the newly formed siloxane-oxyalkylene copolymer. This extra processing step is apparently done because the solvent is too flammable, or too toxic or otherwise unacceptable to be left in the copolymer. For example, see U.S. Pat. Nos. 2,846,458; 3,234,252; 3,280,160; 3,299,112; 3,402,192; 3,505,377; 3,565,845; 3,629,308; 3,657,305; 3,957,843 and 4,184,004. When it is desirable to have the hydrocarbon solvent mixed with the newly formed siloxane-oxyalkylene copolymer, including during the subsequent use to which the siloxane-oxyalkylene copolymer is directed, the hydrocarbon solvent need not be removed. See U.S. Pat. No. 4,381,241.

Less typically, the hydrosilylation reaction between the organohydrogenpolysiloxane reactant and the olefinically substituted polyoxyalkylene reactant is conducted in an oxygen-containing solvent such as an ether, a polyether or a lower alcohol.

For example, U.S. Pat. Nos. 3,280,160 and 3,402,192, noted above, also disclose the preparation of siloxane-oxyalkylene copolymers in n-butyl ether and in a 50/50 mixture of isopropyl alcohol/toluene, respectively. In addition, U.S. Pat. No. 4,122,029 discloses isopropyl alcohol as a suitable solvent for use in the preparation of siloxane-oxyalkylene copolymers. As in the cases where a hydrocarbon solvent was used these oxygen-containing solvents were also removed from the newly formed siloxane-oxyalkylene copolymer, presumably for the same general reason.

U.S. Pat. No. 3,629,308, noted above, also teaches that when one conventionally reacts an organohydrogenpolysiloxane with a polyoxyethylene having an allyl group on one end of the molecule and a hydroxyl group on the other in the presence of a platinum catalyst it is preferable to conduct the reaction in a suitable solvent to reduce the tendency of the newly formed siloxane-oxyalkylene copolymer to gel. Suitable solvents are said to include compounds having the formula $R'O(C_3H_6O)_xH$ where $R'$ is a lower alkyl group and x has a value from 1 to 20. When the resulting siloxane-oxyalkylene copolymer is to be used to stabilize a urethane foam, as disclosed therein, said patent teaches that it is not desirable to isolate the siloxane-oxyalkylene copolymer from such solvents but rather to use the solution thereof.

BRIEF SUMMARY OF THE INVENTION

It is an object of the present invention to provide an improved method for preparing siloxane-oxyalkylene copolymers. It is a further object of this invention to provide improved siloxane-oxyalkylene copolymer compositions. It is also an object of this invention to provide an improved method for preparing siloxane-oxyalkylene copolymers that are suitable for use in personal care compositions as emulsifiers.

To accomplish these objects, and others which may become apparent upon considering the following disclosure and appended claims, this invention teaches that the siloxane-oxyalkylene copolymer is to be prepared by an hydrosilylation reaction between an organohydrogenpolysiloxane and an olefinically substituted polyoxyalkylene, in the presence of a beneficial amount of a saturated higher alcohol. The saturated higher alcohol not only aids in the preparation of the siloxane-oxyalkylene copolymer, it is also left in the copolymer to aid in its subsequent handling and, in some instances, to serve as a necessary component of a composition containing the siloxane-oxyalkylene copolymer.

DETAILED DESCRIPTION OF THE INVENTION

The present invention relates to an improved method for preparing an organopolysiloxane-polyoxyalkylene block copolymer composition, said method comprising reacting an organohydrogenpolysiloxane reactant with an olefinically substituted polyoxyalkylene reactant in the presence of a noble metal-containing hydrosilylation catalyst, the improvement comprising conducting said reacting in the presence of a reaction-improving amount of a saturated higher alcohol. This invention further relates to the compositions obtained by the method of this invention.

In the improved method of this invention the organohydrogenpolysiloxane reactant and the olefinically substituted polyoxyalkylene reactant can be any of those disclosed in the siloxane-oxyalkylene block copolymer art, including those U.S. patents noted above, hereby incorporated by reference.

In the improved method of this invention the organohydrogenpolysiloxane reactant preferably has the general formula $R_aH_bSiO_{(4-a-b)/2}$ wherein R denotes a monovalent hydrocarbon radical free of aliphatic unsaturation, a has a value of from 1 to 2.5, b has a value of from 0.001 to 1 and the sum of $a+b$ has a value of from 1.5 to 3.0.

Illustrative of suitable R radicals are alkyl radicals, such as methyl, ethyl, propyl, butyl, decyl and octadecyl; cycloaliphatic radicals, such as cyclopentyl, cyclohexyl, cyclooctyl and bicyclo[2.2.1]heptyl; aryl radicals such as phenyl, tolyl, xylyl, xenyl and naphthyl and aralkyl radicals, such as benzyl, 2-phenylethyl and 2-phenylpropyl. R is typically the methyl radical.

The organohydrogenpolysiloxane of the above formula can contain any combination of siloxane units selected from the group consisting of $R_3SiO_{1/2}$, $R_2HSiO_{1/2}$, $R_2SiO_{2/2}$, $RHSiO_{2/2}$, $RSiO_{3/2}$, $HSiO_{3/2}$ and $SiO_{4/2}$ provided of course that the organohydrogenpolysiloxane contains sufficient R-containing siloxane units to provide from about 1 to about 2.5 R radicals per silicon atom and sufficient H-containing siloxane units to provide from about 0.001 to 1 silicon-bonded hydrogen atoms per silicon atom and a total of R radicals and silicon-bonded hydrogen atoms of from 1.5 to 3.0, preferably 1.9 to 2.1, per silicon atom in the organohydrogenpolysiloxane.

Illustrative of organohydrogenpolysiloxanes of the formula $R_aH_bSiO_{(4-a-b)/2}$ are cyclic molecules, such as $(RHSiO)_x$ and $(RHSiO)_x(R_2SiO)_y$; linear molecules, such as $R_3SiO(RHSiO)_xSiR_3$, $R_3SiO(RHSiO)_x(R_2SiO)_ySiR_3$, $R_2HSiO(R_2SiO)_ySiR_2H$, $R_2HSiO(RHSiO)_xSiR_2H$ and $R_2HSiO(RHSiO)_x(R_2SiO)_ySiR_2H$ and branched molecules, such as $RSi\{O(R_2SiO)_ySiR_2H\}_3$, $RSi\{O(RHSiO)_x(R_2SiO)_ySiR_3\}_3$, $Si\{O(R_2SiO)_ySiR_2H\}_4$ and $Si\{O(RHSiO)_x(R_2SiO)_ySiR_3\}_4$, where x and y are non-zero numbers.

In the improved methods of this invention the olefinically substituted polyoxyalkylene reactant preferably has the general formula $ZO(C_nH_{2n}O)_mZ$ wherein Z denotes a terminating radical, at least one Z radical having olefinic unsaturation, n is an integer greater than zero and m has an average value of 1 or more.

Illustrative of Z radicals are olefinic radicals, such as $CH_2=CH-$, $CH_2=CHCH_2-$, $CH_2=C(CH_3)-$ and $CH_2=C(CH_3)CH_2-$: other organic radicals, such as alkyl radicals; such as methyl, ethyl, propyl, butyl, hexyl and octyl; acyl radicals, such as $CH_3C(O)-$, $CH_3CH_2C(O)-$, and $C_6H_5C(O)-$; aryl radicals, such as phenyl, naphthyl and furfuryl; and carbalkoxy radicals, such as $CH_3OC(O)-$ and $CH_3CH_2OC(O)-$: and inorganic radicals, such as $(CH_3)_3Si-$ and $H-$.

The value of n in the above formula for the olefinically substituted polyoxyalkylene is an integer greater than zero, such as 1, 2, 3, 4, 6 and 8. Preferably has a value of 2 and/or 3. That is to say, the polyoxyalkylene preferably has the formulae $ZO(C_2H_4O)_mZ$, $ZO(C_3H_6O)_mZ$ or $ZO(C_2H_4O)_{mp}(C_3H_6O)_{mq}Z$ where p and q are each greater than zero but less than 1 and p+q equals 1.

The value of m in the above formulae for the olefinically substituted polyoxyalkylene has an average value of 1 or more, such as 1, 2, 5, 10, 20, 35, 50, 80 and more.

Illustrative of olefinically substituted polyoxyalkylenes having the above formulae are
$CH_2=CHCH_2O(CH_2CH_2O)_{12}C(O)CH_3$,
$CH_2=CHCH_2O(CH_2CH_2O)_{25}(CH_2CH(CH_3)O)_{25}C(O)CH_3$,
$CH_2=CHCH_2O(CH_2CH_2O)_{14}H$,
$CH_2=CHCH_2O(CH_2CH_2O)_7SiMe_3$,
$CH_2=CHCH_2O(CH_2CH_2O)_{50}CH_3$ and
$CH_2=CHCH_2O(CH_2CH_2O)_2CH_2CH=CH_2$.

In the improved method of this invention the hydrosilylation reaction between an organohydrogenpolysiloxane reactant and an olefinically substituted polyoxyalkylene reactant is catalyzed by a catalytic amount of a noble metal-containing catalyst. Suitable noble metal-containing catalysts are well known and include platinum-, palladium- and rhodium-containing catalysts, such as platinum on a carrier, such as alumina or charcoal, finely divided platinum and, preferably, chloroplatinic acid.

In the improved method of this invention the relative amounts of reactants may vary widely, e.g. from a stoichiometric excess of either reactant to equivalent amounts of reactants. That is to say, the reactants can range in amounts from excess organohydrogenpolysiloxane (more than one silicon-bonded hydrogen for every olefinic radical in the polyoxyalkylene), whereupon the resulting siloxane-oxyalkylene copolymer will contain unreacted SiH groups, to equivalent amounts of reactants (SiH/C=C=1), whereupon the resulting siloxane-oxyalkylene copolymer is substantially free of SiH groups and olefinic radicals, to excess olefinically substituted polyoxyalkylene (SiH/C=C<1), whereupon the resulting siloxane-oxyalkylene copolymer contains unreacted polyoxyalkylene.

In the improved method of this invention the improvement comprises conducting the above-delineated hydrosilylation reaction in a reaction-improving amount of a saturated higher alcohol.

By reaction-improving amount it is meant any amount of saturated higher alcohol that will improve one or more aspects of the reaction, such as the reaction rate, the reaction yield, the reaction specificity, the reaction processing or the reaction product processing. For example, when isostearyl alcohol is used, it has been found that the use of about 10 percent by weight, based on the weight of organohydrogenpolysiloxane plus olefinically substituted polyoxyalkylene, of the alcohol will aid in the handling of the reactants and the mutual solubility of the reactants. As another example, as little as 4 percent by weight of isostearyl alcohol provides a surfactant for preparing flexible polyurethane foam which is equivalent to the surfactant obtained when isopropyl alcohol is used as the solvent and is subsequently removed from the surfactant before it is used in a polyurethane foam composition. Of course, amounts of saturated higher alcohol larger than 10 percent can be used if desired. The compositions of this invention thus contain a saturated higher alcohol, preferably at least about 4 percent by weight thereof.

Any saturated higher alcohol that is a liquid at the reaction conditions of the hydrosilylation reaction can be used in the method of this invention. Preferably the saturated higher alcohol is a liquid at room temperature, i.e. 15° to 35° C.

By saturated higher alcohol it is meant any alcohol which has at least 8 carbon atoms and is free of aliphatic unsaturation. Saturated higher alcohols are well known and need no further description here; some are commercially available. They can be prepared by the reduction of fat acids.

The saturated higher alcohol can be a single isomer, such as octyl alcohol, or a mixture of isomers, such as a mixture of stearyl alcohol and isostearyl alcohol, or a mixture of homologs, such as a mixture of myristyl alcohol and lauryl alcohol.

An exemplary saturated higher alcohol is isostearyl alcohol because it is a liquid at around 25° C., it is readily available in commercial quantities and in commercial purities and it is an acceptable, and frequently desirable, component of a siloxane-oxyalkylene block copolymer composition to be used in the formulation of personal care formulations.

The improved method of this invention is further illustrated and explained, but not limited, by the following examples. Parts and percentages are by weight unless otherwise stated. Me denotes the methyl radical, IPA denotes isopropyl alcohol and ISA denotes isostearyl alcohol.

EXAMPLE 1

A mixture of 40 parts of $Me_3SiO(MeHSiO)_{40}SiMe_3$ and 0.3 parts of a 0.5% solution of $H_2PtCl_6.6H_2O$ in isopropanol was placed under a nitrogen atmosphere and heated to 85° C. Approximately 92 parts of dodecene having an olefinic activity of 91% were slowly added to the above mixture so that the temperature of the reaction mixture did not exceed 140° C. Isostearyl alcohol, 20.75 parts, (12.1 parts per 100 parts of organohydrogenpolysiloxane plus polyoxyalkylene) was then added to the organohydrogenpolysiloxane along with another 0.33 part portion of the platinum-containing solution. Forty parts of $CH_2=CHCH_2(OCH_2CH_2)_{19}(OCHCH_3CH_2)_{19}OH$ were then added to the reaction mixture and the resulting mixture was heated at 140° C. for 45 minutes. Another 0.33 part portion of platinum-containing solution and 38 parts of the 91% active dodecene were then added and the resulting mixture was heated for 1 hour at 140° C. and then cooled to room temperature under the nitrogen atmosphere. The resulting siloxane-oxyalkylene copolymer solution had a viscosity of 3130 centistokes.

EXAMPLE 2

This example illustrates the beneficial effect of the method of this invention on the viscosity of and on the presence of gels in, a siloxane oxyalkylene copolymer prepared by a hydrosilylation reaction.

The preparation of Example 1 was repeated except that 30 parts of $CH_2=CHCH_2(OCH_2CH_2)_{19}(OCHCH_3CH_2)_{19}OH$ were used instead of 40 parts. The resulting siloxane-oxyalkylene copolymer solution had a viscosity of 1648 centipoise and contained no gels.

To compare the method of the present invention with a prior art method, which uses isopropyl alcohol, the above preparation was repeated except that isopropyl alcohol, instead of isostearyl alcohol, was used as the reaction solvent and, in a final step, removed from the reactive mixture by vacuum distillation at 90° C. and 100 mm of Hg pressure. A siloxane-oxyalkylene copolymer having a viscosity of 36,320 centipoise and containing some gels was obtained. This copolymer was then mixed with 20 parts of isostearyl alcohol and the viscosity of the resulting solution was measured. The value obtained, 3712 centipoise, was directly comparable with the value obtained by the method of this invention, i.e. 1648 centipoise, because the concentration of siloxane-oxyalkylene copolymer in isostearyl alcohol was the same in each case. The lower viscosity for the solution of copolymer in isostearyl alcohol that was obtained by the method of this invention was attributed to the absence of gels in the siloxane-oxyalkylene copolymer.

EXAMPLE 3

A well-stirred mixture of 83 parts of an olefinically substituted polyoxyalkylene having the average formula $CH_2=CHCH_2(OCH_2CH_2)_{18}(OCHCH_3CH_2)_{18}O_2CCH_3$, 17 parts of an organohydrogenpolysiloxane having the average formula $Me_3SiO(Me_2SiO)_{103}(MeHSiO)_9SiMe_3$ and 9.8 parts of isostearyl alcohol was degassed at reduced pressure, placed under a nitrogen atmosphere and heated to 75° C. A solution of $H_2PtCl_6.6H_2O$ in the polyoxyalkylene was added to the heated mixture in sufficient amount to provide 0.0018 parts of platinum. The heat source was removed and the exothermic hydrosilylation reaction was allowed to proceed until no further temperature increase was noted. Heat was then added to the mixture as needed to keep its temperature at 85° C. for 1 hour.

The above reaction was twice repeated except that 4.2 parts and 2 parts, respectively, of isostearyl alcohol were used instead of 9.8 parts.

The above reaction was also repeated except that no isostearyl alcohol was used in the reaction mixture.

The above reaction was also conducted in 32.6 parts of isopropyl alcohol, instead of 9.8 parts of isostearyl alcohol, as follows. The mixture of polyoxyalkylene, siloxane and isopropyl alcohol was heated to 75° C., catalyzed with 0.0006 parts of the platinum, refluxed for 30 minutes and then devolatilized at 10 mm of Hg pressure to a temperature of 100° C. to remove the isopropyl alcohol. The devolatilized reaction product was cooled to room temperature under reduced pressure.

The above-prepared reaction products were evaluated as surfactants in a polyurethane foam composition in the following manner.

A mixture of 107.8 parts of a polyol base, 0.6 parts of the above prepared surfactant (not counting isostearyl alcohol) and 0.4 parts of dibutyl tin dilaurate were thoroughly mixed. To the above mixture was added 53.1 parts of toluene diisocyanate and the resulting mixture was mixed for six seconds and 142 parts thereof were poured into an 83 ounce paper cup. The mixture was allowed to foam and rise to maximum height and was then cured at 200° C. for 20 minutes.

The cured foam was evaluated by measuring foam height, air flow through the foam and foam cell quality in the well known manner. The results, shown in the Table, show that the surfactant that was made by the method of this invention was equal or superior to the surfactant that was made without a reaction solvent and equal or superior to the surfactant that was made with isopropyl alcohol as a reaction solvent, according to one or more test criteria.

TABLE

| Surfactant Solvent | | Polyurethane Foam Evaluation | | |
|---|---|---|---|---|
| Amount[1] | Identity | Foam Height[2] | Airflow[3] | Quality[4] |
| 32.6 | IPA | 9 3/16 | 5.8 | A |
| 9.8 | ISA | 9 3/16 | 6.4 | A |
| 4.2 | ISA | 9 | 6.6 | A |
| 2.0 | ISA | 8 10/16 | 6.6 | X |
| None | | 8 8/16 | 6.9 | X |

[1] parts per 100 parts of polysiloxane + polyoxyalkylene
[2] inches ± 1/16"
[3] ft$^3$/min. ± 0.2
[4] A = good foam
X = top blow That which is claimed is:

1. In the method for preparing an organopolysiloxane-polyoxyalkylene copolymer composition, said method comprising reacting an organohydrogenpolysiloxane reactant with an olefinically substituted polyoxyalkylene reactant in the presence of a platinum-containing hydrosilylation catalyst, the improvement comprising conducting said reacting in the presence of a reaction-improving amount of an alcohol which has at least 8 carbon atoms and is free of aliphatic unsaturation and allowing said alcohol to remain with the composition after said reacting.

2. A method according to claim 1 wherein the alcohol is isostearyl alcohol.

3. A method according to claim 2 wherein the amount of isostearyl alcohol has a value of at least about 4 percent by weight, based on the total weight of said reactants.

4. The composition obtained by the method of claim 2.

5. The composition obtained by the method of claim 3.

6. A composition consisting essentially of an organopolysiloxane-polyoxyalkylene block copolymer and isostearyl alcohol, the amount of said alcohol being at least about 4 percent by weight, based on the total weight of the composition.

* * * * *